United States Patent
Ha et al.

(10) Patent No.: US 11,148,984 B2
(45) Date of Patent: Oct. 19, 2021

(54) METHOD OF REGENERATING ZEOLITE CATALYST FOR AROMATIZATION OF ACETYLENE BY PLASMA TREATMENT

(71) Applicant: Industry-University Cooperation Foundation Sogang University, Seoul (KR)

(72) Inventors: Kyoung-Su Ha, Hanam-si (KR); MahnJung Kim, Seoul (KR); Juchan Kim, Seoul (KR); Jaekwon Jeoung, Seoul (KR)

(73) Assignee: Industry-University Cooperation Foundation Sogang University, Seoul (KR)

(*) Notice: Subject to any disclaimer, the term of this patent is extended or adjusted under 35 U.S.C. 154(b) by 232 days.

(21) Appl. No.: 16/288,995

(22) Filed: Feb. 28, 2019

(65) Prior Publication Data

US 2019/0262816 A1 Aug. 29, 2019

(30) Foreign Application Priority Data

Feb. 28, 2018 (KR) .................. 10-2018-0024839

(51) Int. Cl.

| C07C 2/48 | (2006.01) |
|---|---|
| B01J 29/90 | (2006.01) |
| H05H 1/24 | (2006.01) |
| B01J 29/40 | (2006.01) |
| C07C 15/06 | (2006.01) |

(Continued)

(52) U.S. Cl.

CPC ............. *C07C 2/48* (2013.01); *B01J 29/40* (2013.01); *B01J 29/90* (2013.01); *H05H 1/2406* (2013.01); *C07C 15/04* (2013.01); *C07C 15/06* (2013.01); *C07C 15/08* (2013.01); *C07C 2529/40* (2013.01); *H05H 1/2443* (2021.05)

(58) Field of Classification Search
None
See application file for complete search history.

(56) References Cited

U.S. PATENT DOCUMENTS

| 4,424,401 A | 1/1984 | White et al. |
| 2016/0090334 A1* | 3/2016 | Hershkowitz ........... C07C 2/864 585/322 |

OTHER PUBLICATIONS

Zhang et al. "Plasma methane conversion in the presence of carbon dioxide using dielectric-barrier discharges" Fuel Processing Technology 83 (2003) 101-109 (Year: 2003).*

(Continued)

*Primary Examiner* — Philip Y Louie
*Assistant Examiner* — Alyssa L Cepluch
(74) *Attorney, Agent, or Firm* — Seed Intellectual Property Law Group LLP

(57) ABSTRACT

The present invention relates to a method of preparing an aromatic compound from acetylene, which includes synthesizing an aromatic compound from an acetylene-containing reactant gas in the presence of a zeolite catalyst for the aromatization of acetylene, and subjecting the zeolite catalyst deactivated by the coke formed in the aromatization of acetylene, to plasma treatment at ambient temperature and pressure so as to selectively remove the external cokes and partial internal coke, thereby regenerating the zeolite catalyst; a method of regenerating the zeolite catalyst used in the aromatization of acetylene by plasma treatment; and a regenerated zeolite catalyst for the aromatization of acetylene, prepared thereof.

9 Claims, 6 Drawing Sheets

(51) Int. Cl.
*C07C 15/08* (2006.01)
*C07C 15/04* (2006.01)

(56) References Cited

OTHER PUBLICATIONS

Fan et al., "Regeneration of the HZSM-5 zeolite deactivated in the upgrading of bio-oil via non-thermal plasma injection (NTPI) technology," *Journal of Analytical and Applied Pyrolysis* 111:209-215, 2015.
Liu et al., "Nonoxidative Methane Conversion to Acetylene over Zeolite in a Low Temperature Plasma," *Journal of Catalysis* 179:326-334, 1998.
Kim et al. "*Regeneration of Deactivated H-ZSM-5 for Aromatization by Dielectric Barrier Discharge Plasma*" Applied Catalysis A, General (2019), 36 pages.

* cited by examiner

[FIG. 1]
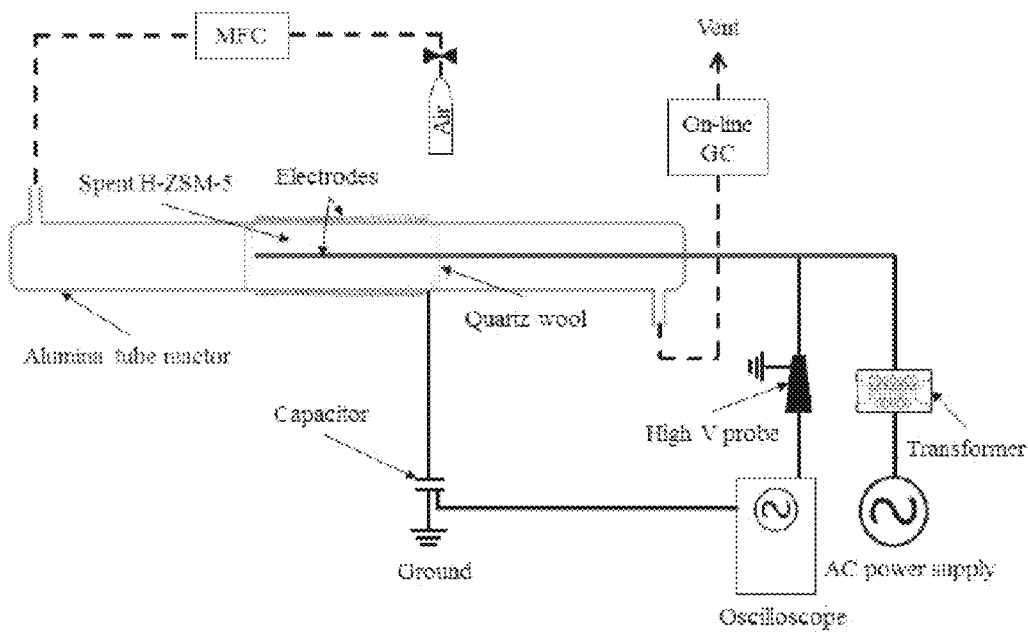
[FIG. 2]
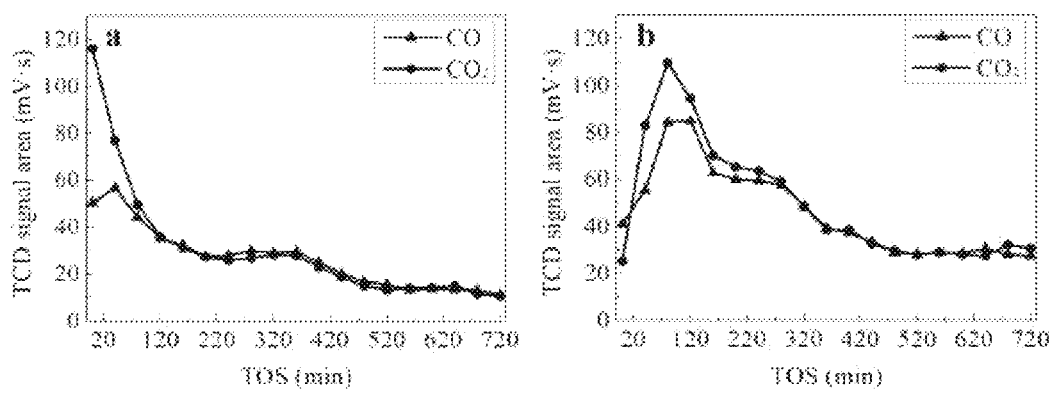

[FIG. 3]
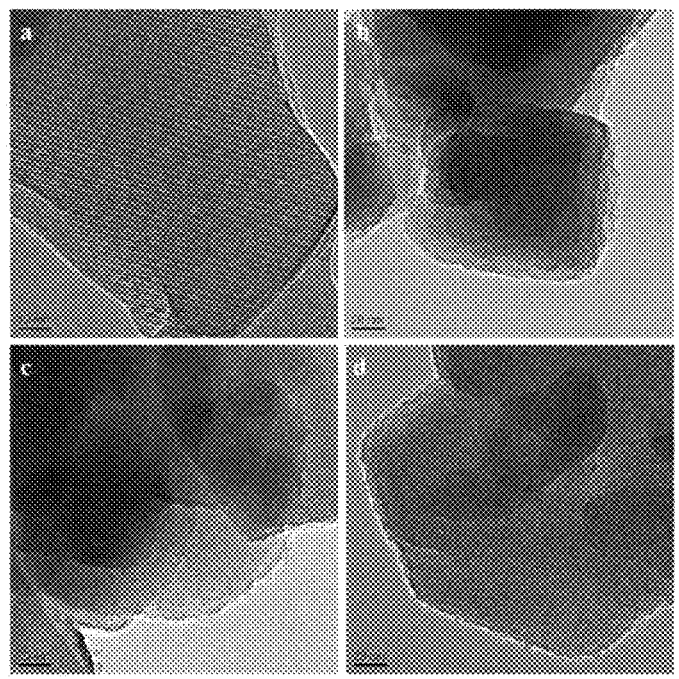
[FIG. 4]
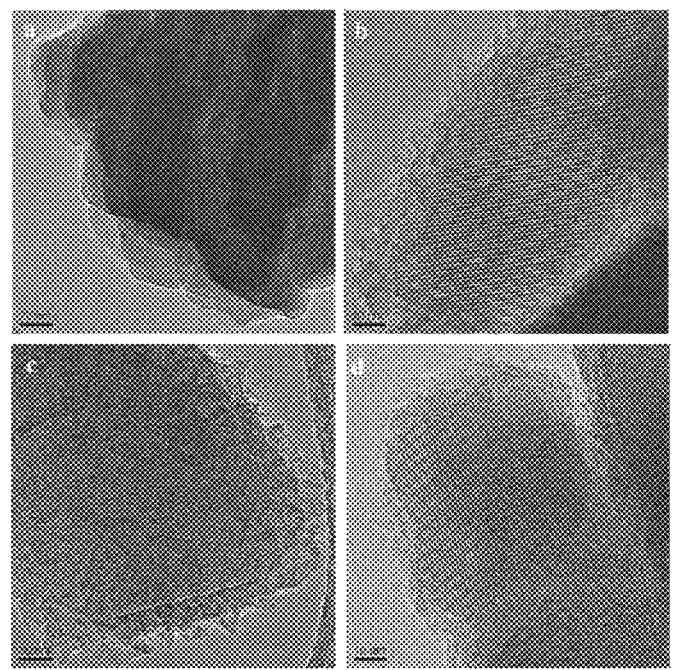

[FIG. 5]
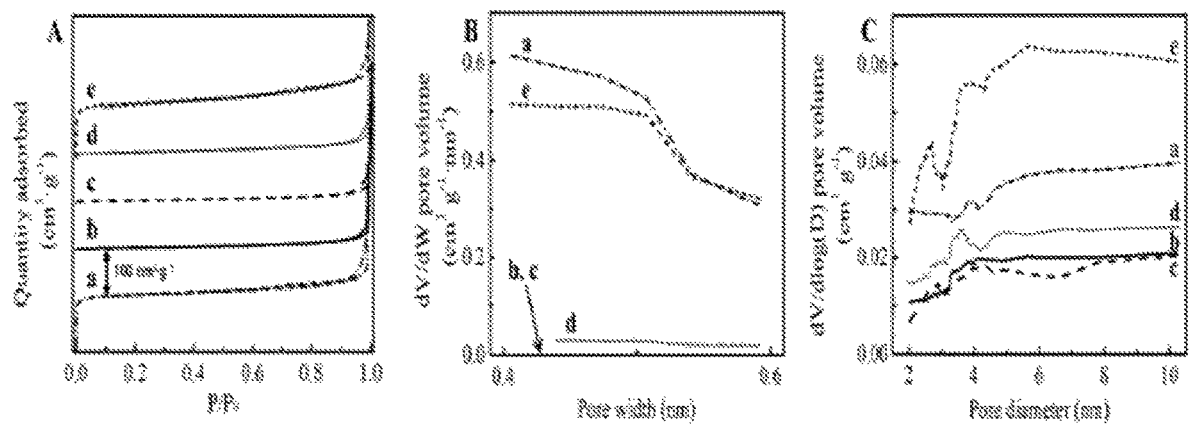
[FIG. 6]
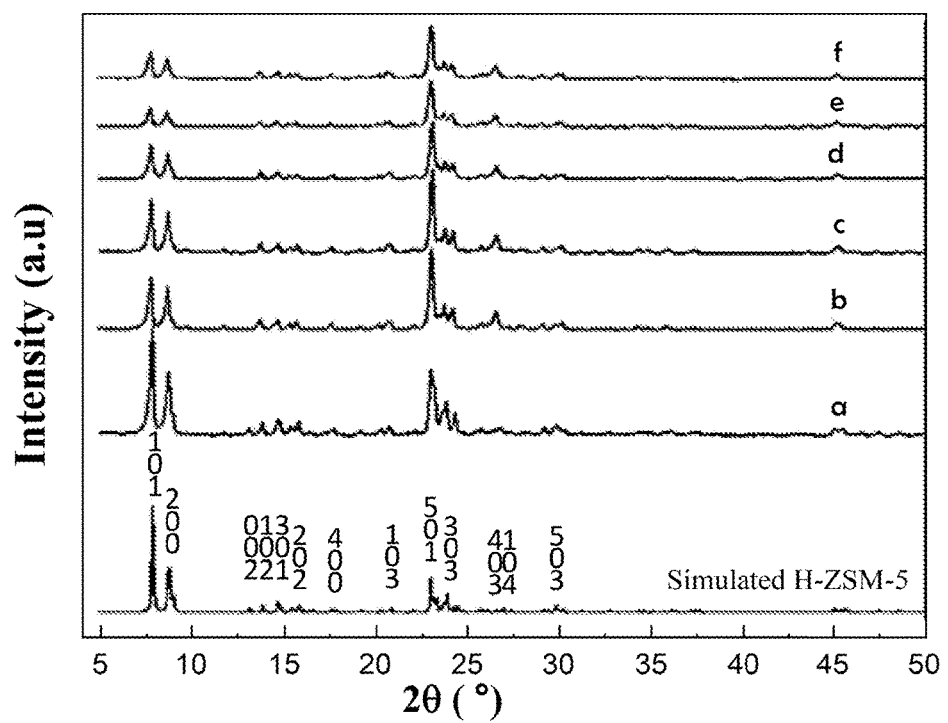

[FIG. 7]
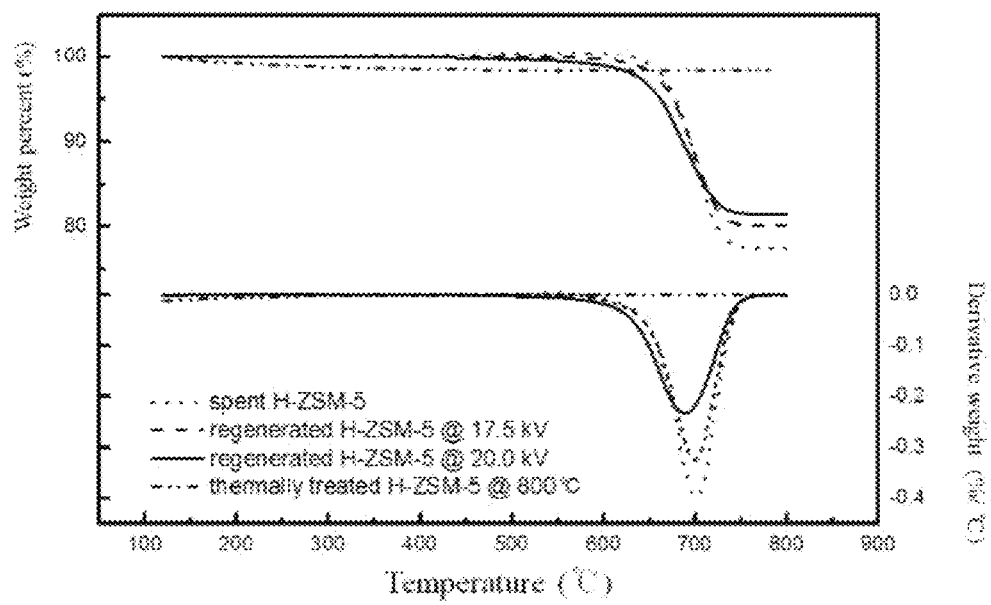
[FIG. 8]
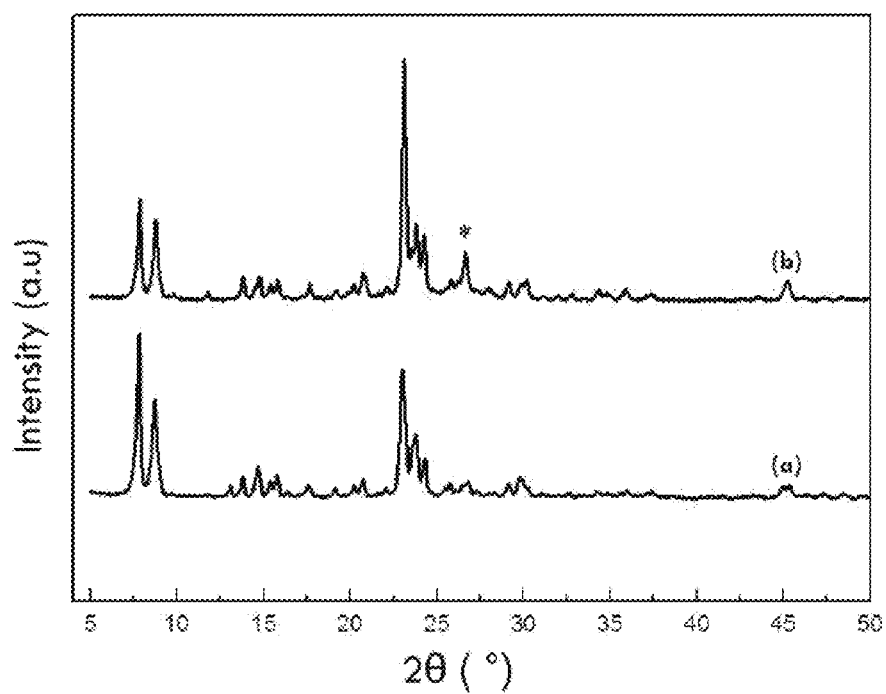

[FIG. 9]
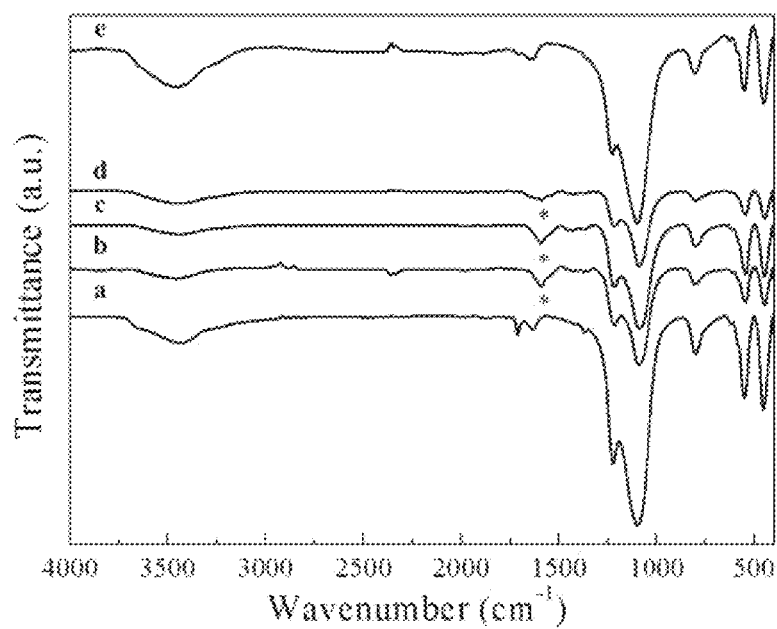
[FIG. 10]
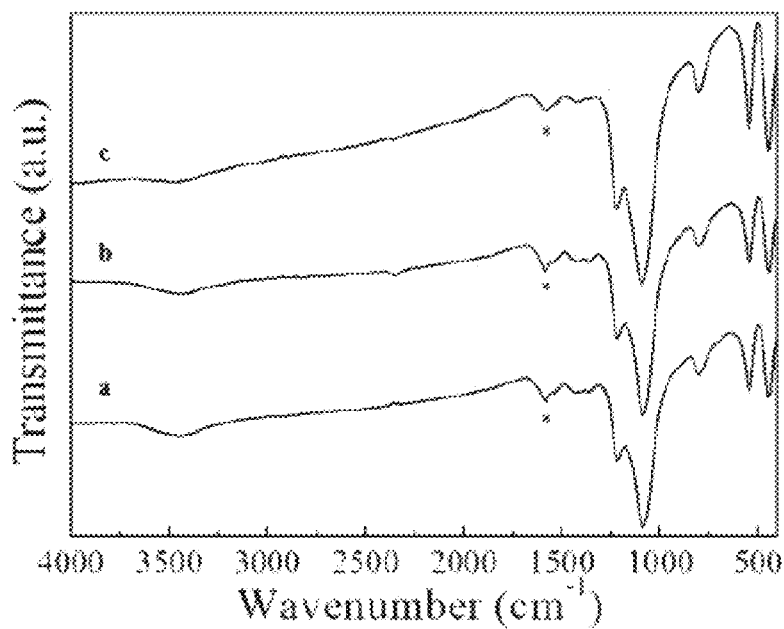

[FIG. 11]
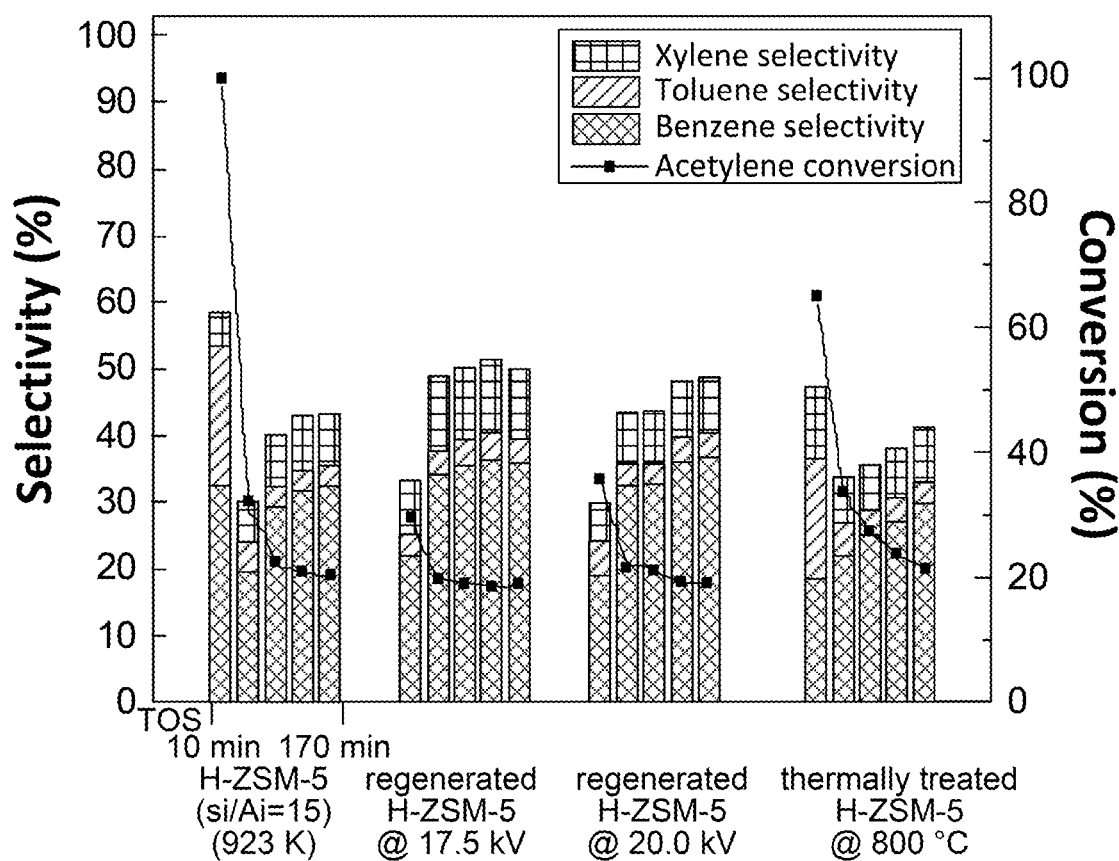

METHOD OF REGENERATING ZEOLITE CATALYST FOR AROMATIZATION OF ACETYLENE BY PLASMA TREATMENT

TECHNICAL FIELD

The present invention relates to a method of preparing an aromatic compound from acetylene, which includes synthesizing an aromatic compound from an acetylene-containing reactant gas in the presence of a zeolite catalyst for the aromatization of acetylene, and subjecting the zeolite catalyst deactivated by the coke formed in the aromatization of acetylene, to plasma treatment at ambient temperature and pressure so as to selectively remove the external cokes and partial internal coke, thereby regenerating the zeolite catalyst; a method of regenerating the zeolite catalyst used in the aromatization of acetylene by plasma treatment; and a regenerated zeolite catalyst for the aromatization of acetylene, prepared thereof.

BACKGROUND ART

Conventionally, aromatic compounds have been prepared from petroleum-derived materials and even now are obtained as such. The aromatic chemical industry has been established using petroleum-derived materials as raw materials. Specifically, various aromatic compounds are produced in the process of distilling various distillates by petroleum refining and reforming distilled naphtha materials. Many types of aromatic compounds have been utilized as a basic aromatic compound in the chemical industry, and among them, benzene, toluene, xylene, etc. (hereinafter, BTX) distillates are in the highest demand and they are the high value-added aromatic compounds with high utilization. They have been widely utilized as styrene monomers, terephthalate monomers, solvent, etc. and have also been used in synthesizing final polymeric compounds such as PET and polystyrene.

As is well known, although petroleum is the most important raw material in the chemical industry, its mining reserves are relatively short to be depleted within decades. Additionally, due to supply and demand or geopolitical issues of petroleum-producing countries and major petroleum-consuming countries, the price of petroleum as a raw material is very volatile.

To resolve the problems of raw materials, efforts have been continuously made to utilize methane resources that are more abundant in reserves and yet can be supplied from places not too far from the markets. As part of this effort, a method for synthesizing aromatic compounds from methane by a single step has recently been in the spotlight. However, despite the high potential, such a method often results in severe deactivation as well as low yield, and thus has not yet been commercialized. A more realistic synthetic route may be to first produce synthetic gas from methane, to synthesize methanol therefrom, and to conduct methanol-to-olefin (MTO), followed by aromatization of olefins such as ethylene and propylene. However, even if such a method is technically feasible, its commercialization is still difficult because securing techno-economic feasibility is challenging due to a number of steps involved in synthesis and large energy consumption. Meanwhile, hydrocarbons that are more reactive than methane, such as propane among gas resources is more likely to be used and commercialization techniques are already being used in the market.

As a catalyst for the aromatization of such hydrocarbon compounds, a zeolite catalyst (so-called a solid acid) is most widely used. Zeolite catalysts are porous materials with micro-level pores, and have active sites inside the pores which have reactive acid sites. Hydrocarbons are attached to these active sites to undergo oligomerization and cyclization and ultimately aromatic compounds such as benzene, toluene, and xylene are synthesized therefrom. As described above, since zeolites have a structure in which micro-scale pores are arranged, it is possible to observe that the selectivity of certain aromatic compounds increases due to the shape of the pores.

Meanwhile, since the aromatization is conventionally conducted at high temperature, it accompanies the deactivation of a catalyst due to excessive side reactions. As the reactions such as dehydrogenation, cracking, polymerization, etc., become severer, carbon accumulation is by-produced, and these carbon accumulation degrade the activity of the catalyst by blocking the active sites. Usually, it is very difficult to completely avoid or remove such a process of catalyst deactivation, although there is a difference in degree or speed of catalyst deactivation, since the process is carried out due to a thermodynamic reason. Therefore, as an alternative thereto, research is in progress to improve the selectivity for aromatic compounds by enabling the synthesis at a relatively low reaction temperature by using metals supported onto zeolite.

DISCLOSURE

Technical Problem

In carrying out a BTX synthesis process by the aromatization of acetylene using a conventional zeolite catalyst, the present inventors have made efforts to discover a method for regenerating a catalyst by recovering the activity of the catalyst deactivated by coke formation, as well as avoiding excessive wasting of reactants due to side reactions when using the regenerated catalyst. As a result, they have found that in the case of treating the catalyst deactivated in the aromatization of acetylene, with plasma by applying a high voltage of 15 kV or more at ambient temperature and pressure, the deactivated catalyst could be regenerated in such a way that coke, which has been formed site-selectively, is partially removed and when performing the $2^{nd}$ run of aromatization, the plasma treated and regenerated catalyst could suppress side reactions by adjusting a reaction speed, thereby avoiding the excess consumption of reactants by the side reactions and improve the BTX selectivity through a pore size adjustment. The present invention is based on the above findings.

Technical Solution

A first aspect of the present invention provides a method of preparing an aromatic compound from acetylene, which comprises:

a first step of synthesizing an aromatic compound from an acetylene-containing reactant gas in the presence of a zeolite catalyst for the aromatization of acetylene, thereby forming internal coke inside the micropores of the zeolite catalyst and external coke in the space between catalyst particles, outer surface of the particles, and/or empty space other than the micropores;

a second step of (i) locating the zeolite catalyst used in the first step between a high voltage electrode and a ground electrode into a plasma reactor, in which the high voltage electrode is provided inside of the reactor and the ground electrode is provided outside of the reactor, and (ii) treating with the plasma generated by applying a voltage at the kV level to the high voltage electrode, so as to selectively remove 25 wt % to 50 wt % of the total amount of the external coke and 0.5 wt % to 10 wt % of the total amount of the internal coke from the zeolite catalyst; and a third step of repeatedly performing the first step using, as a zeolite catalyst for the aromatization of acetylene, the plasma-treated zeolite catalyst of the second step.

A second aspect of the present invention provides a method of regenerating a zeolite catalyst for the aromatization of acetylene used in the synthesis of an aromatic compound from an acetylene-containing reactant gas, in which internal coke is formed inside the micropores of the zeolite catalyst and external coke is formed in the space between catalyst particles, outer surface of the particles, and/or empty space other than the micropores, wherein the method comprises:

(i) locating the used zeolite catalyst between a high voltage electrode and a ground electrode into a plasma reactor, in which the high voltage electrode is provided inside of the reactor and the ground electrode is provided outside of the reactor, and (ii) treating with the plasma generated by applying a voltage at the kV level to the high voltage electrode, so as to selectively remove 25 wt % to 50 wt % of the total amount of the external coke and 0.5 wt % to 10 wt % of the total amount of the internal coke from the zeolite catalyst.

A third aspect of the present invention provides a zeolite catalyst for the aromatization of acetylene regenerated by the method of the second aspect.

A fourth aspect of the present invention provides a dielectic barrier discharge (DBD) plasma reactor for regenerating a zeolite catalyst for the aromatization of acetylene used in the synthesis of an aromatic compound from an acetylene-containing reactant gas, in which internal coke is formed inside the micropores of the zeolite catalyst and external coke is formed in the space between catalyst particles, outer surface of the particles, and/or empty space other than the micropores, wherein the dielectic barrier discharge plasma reactor comprises:

a channel-type container made of a dielectric material, which is able to receive the zeolite catalyst used in the aromatization of acetylene;

a ground electrode, which is located on the outer wall of the channel-type container;

a high voltage electrode, which is inserted into the zeolite catalyst received inside the channel-type container to be spatially separated in parallel from the channel-type container made of a dielectric material, and which has a higher voltage than the ground voltage;

a fixing part, which fixes the used zeolite catalyst, that is received inside the channel-type container, in a predetermined area; and a power supply part, which provides a controlled voltage to the high voltage electrode, so as to selectively remove 25 wt % to 50 wt % of the total amount of the external coke and 0.5 wt % to 10 wt % of the total amount of the internal coke from the used zeolite catalyst.

Hereinafter, the present invention is described in more detail.

The term "aromatic compounds', as used herein, also called arenes or aromatics, may refer to compounds that contain a conjugated planar ring structure with delocalized pi (7c) electron clouds including alternating single and double bonds. Typical aromatic compounds include benzene, and toluene and xylene, which include one or two substituted methyl groups in the benzene ring, respectively.

These aromatic compounds are extensively used across the chemical industry, as well as for the synthesis of high value-added polymeric compounds such as PET and polyester, and they can be prepared by the cyclization of acetylene or the dehydrogenation of saturated hydrocarbons. Among those methods of preparing aromatic compounds, in a method of preparing aromatic compounds using acetylene as a raw material, the aromatic compounds may be synthesized using a solid acid catalyst such as zeolite catalyst, more specifically H-ZSM-5. Meanwhile, as the reaction is normally conducted at high temperature of 600° C. or higher, it results in acceleration of side reactions such as dehydrogenation, cracking, and polymerization which produce and accumulate unwanted by-products of carbon materials. The accumulation of the carbon materials not only deactivate catalysts by covering the active sites of the catalysts but also exert undesirable influence on mass balance and yield of the products. Hydrocarbons produced by the side reactions above are called coke and the phenomenon of coke formation is called coking. Since such a coking is carried out based on a thermodynamic reason, the degree and/or speed of the coke formation may be adjusted but it is very difficult to completely avoid or remove it.

The present invention was designed to overcome the problems encountered with the conventional methods of regenerating catalysts deactivated by coke formation by thermal treatment at high temperature in that although the most of the cokes formed can be removed but the stability of the catalyst may be degraded and even the original structure of the catalyst may be damaged thus deteriorating the activity of the catalyst, and in addition, not enabling repeated use of the regenerated catalyst. The present invention is based on the discovery that, in a method of preparing aromatic compounds by repetitive aromatization runs of acetylene using a regenerated zeolite catalyst by coke removal although deactivated by coke formation in the previous aromatization of acetylene, selectively removing only an appropriate level of the coke allows to adjust the reaction speed in the following $2^{nd}$ run or subsequent reactions and thus excessive wasting of acetylene of raw materials can be avoided and additional coking can be delayed.

The method of preparing an aromatic compound from acetylene of the present invention comprises:

a first step of synthesizing an aromatic compound from an acetylene-containing reactant gas in the presence of a zeolite catalyst for the aromatization of acetylene, thereby forming internal coke inside the micropores of the zeolite catalyst and external coke in the space between catalyst particles, outer surface of the particles, and/or empty space other than the micropores;

a second step of (i) locating the zeolite catalyst used in the first step between a high voltage electrode and a ground electrode into a plasma reactor, in which the high voltage electrode is provided inside of the reactor and the ground electrode is provided outside of the reactor, and (ii) treating with the plasma generated by applying a voltage at the kV level to the high voltage electrode, so as to selectively remove 25 wt % to 50 wt % of the total amount of the external coke and 0.5 wt % to 10 wt % of the total amount of the internal coke from the zeolite catalyst; and a third step of repeatedly performing the first step using, as a zeolite catalyst for the aromatization of acetylene, the plasma-treated zeolite catalyst of the second step.

In the preparation method of the present invention, the first step may be performed using the method of preparing aromatic compounds in the presence of a zeolite catalyst using acetylene as a raw material, for example, at 600° C. or higher, for example, at 650° C. under the atmospheric pressure. In particular, the zeolite catalyst may be used in combination with a diluent, such as alumina, with about a 4-fold weight of the zeolite catalyst. In addition, for an acetylene-containing reactant gas, mixture gas of hydrogen and nitrogen may be provided and mixed to have a 2 to 7 fold weight of the amount of acetylene to be used, respectively, but the amount of the mixture gas is not limited thereto. The acetylene-containing reactant gas may be provided at a gas hourly space velocity (GHSV) of 15,000 mL/$g_{cat}$·h to 30,000 mL/$g_{cat}$·h based on acetylene, but the GHSV of the acetylene-containing reactant gas is not limited thereto.

For example, in the preparation method of the present invention, the second step may be performed by applying a voltage in the range of 7 kV to 50 kV to the high voltage electrode. Specifically, a voltage in the range of 15 kV to 30 kV may be applied to perform the second step, but the voltage application is not limited thereto. However, a voltage applied less than 7 kV, that is, in the case of less than breakdown voltage, the plasma may not be generated because sufficient energy generating the plasma is not given to the dielectric, and as a result, the coke removal efficiency may be remarkably low. Meanwhile, application of a high voltage of over 50 kV is physically limited and it could result in wasting energy more than required.

The second step of regenerating the used and deactivated catalyst by plasma treatment, as a step performing to restore the activity of the catalyst by removing the coke, may be performed at low temperature in the range of 1° C. to 35° C. with air flows. For example, it may be performed at ambient temperature in the range of 15° C. to 25° C., but the temperature is not limited thereto. As a result, since the second step can be performed at a relatively low temperature to remove the coke and regenerate the catalyst, the problems of the conventional technology can be resolved, in which the conventional regeneration of a catalyst by thermal treatment at high temperature would damage the structure of the catalyst itself and deteriorate the stability of the catalyst.

In particular, the second step may be performed at ambient temperature, but the temperature is not limited thereto. For instance, a pressure that generates plasma under the condition of an applied voltage according to the Paschen's Law, which indicates the relationship between an applied voltage and a breakdown voltage, may be selected without limitation. That is, a pressure may be selected within a range enabling plasma generation according to the type of a dielectric and a voltage applied to the dielectric.

Furthermore, in the preparation method for an aromatic compound of the present invention, after the third step of synthesizing an aromatic compound from acetylene using a catalyst regenerated by plasma treatment, a 2-n step and a 3-n step, which are the same as the second step and the third step, respectively, may be repeatedly performed n times, in which n is a positive integer, but n is not limited thereto.

In case of regenerating a deactivated catalyst by plasma treatment at ambient temperature and pressure, although the initial reaction speed of the regenerated catalyst may be reduced due to the remaining coke, the side reactions may be remarkably reduced, which may significantly delay the speed of additional coke formation and prevent excessive wasting of acetylene and as a result, during an extended period of time with an adjusted speed, an aromatic compound maybe prepared with a high selectivity, since the size of micropores inside the catalyst may be adjusted by the remaining coke which increases the selectivity for BTX products. In addition, since it does not undergo a thermal treatment process which threats the stability of a catalyst, by performing the regeneration and the aromatization repeatedly, the amount of an aromatic compound that can be produced by a unit catalyst, can be significantly increased.

In the present invention, the cokes removed by plasma treatment in the process of regenerating a catalyst by the coke removal may be graphitic carbonaceous materials. In a specific embodiment of the present invention, by X-ray diffraction analysis, it was confirmed that the peak generated by graphitic carbonaceous materials, which were not present in a catalyst before performing the aromatization of acetylene, appeared in a catalyst that was used in the reaction, and was partially reduced by the plasma treatment and its degree was dependent on the level of the applied voltage.

As described above, the present invention is characterized in that when the coke formed is removed for regenerating the deactivated catalyst, by plasma generated under mild conditions of ambient temperature and pressure, as a result, the internal coke formed inside the micropores of the deactivated catalyst are partially removed while mainly removing a large amount of the external coke formed in parts other than the micropores inside, selectively. As a result, the plasma-treated zeolite catalyst can comprise cokes that remain at a ratio in the range of 0.5 to 0.7 (the amount of external coke/the amount of internal coke), but the ratio is not limited thereto. In a specific embodiment of the present invention, a ratio of the amount of external coke/the amount of internal coke for the spent catalyst which was not regenerated by the plasma treatment was as high as 0.84, but after the regeneration of the catalyst by the plasma treatment, the ratio went below 0.6, specifically as low as 0.57 and 0.58, but the ratio was maintained at a significantly high level compared to the regenerated catalyst by thermal treatment which showed a value of 0.

In the present invention, the plasma-treated zeolite catalyst of the second step may show 20% to 45% of acetylene conversion for the first 10 minutes of a reaction in the third step. This is in contrast to the result of a fresh catalyst, which has not been used and regenerated, i.e., used for the first time after the preparation of a catalyst, showing very high acetylene conversion of about 95% for the first 10 minutes of the reaction. For example, as described above, while the fresh catalyst showed a very high acetylene conversion as well as a high BTX selectivity for the first 10 minutes of the reaction, these values rapidly dropped with the reaction time and the final BTX selectivity was not very high. Meanwhile, in the case where the catalyst regenerated by the method of the present invention was used, the acetylene conversion and the BTX selectivity for the first 10 minutes of a reaction were lower than the fresh catalyst, but the conversion reduction was significantly reduced with the reaction time and the BTX selectivity was increased and maintained at a higher level (FIG. 11).

In particular, the zeolite catalyst regenerated by the second step may show a BTX selectivity of 40% to 55% in an additional aromatization of acetylene (i.e., a reaction of the third step), but the BTX selectivity is not limited thereto.

Specifically, among these BTX compounds, the selectivity may be in the range of 30% to 40% for benzene, 3% to 4.5% for toluene, and/or 7% to 12% for xylene, but the BTX selectivity is not limited thereto.

In a specific embodiment of the present invention, each catalyst regenerated by plasma treatment at 17.5 kV and 20.0 kV, respectively, was re-used as a catalyst for the aromatization of acetylene to measure the acetylene conversion along with the total BTX selectivity and the selectivity of an individual BTX compound and compared the results of the fresh catalyst and the regenerated catalyst by thermal treatment at high temperature of 800° C. as Comparative Examples. As a result, in the case of the catalyst regenerated by thermal treatment at high temperature of 800° C., it showed a similar level and pattern of reactivity to the fresh catalyst except the acetylene conversion and BTX selectivity somewhat reduced compared to the fresh catalyst for the first 10 minutes of the reaction. However, in the case of the reaction of the present invention where the catalyst regenerated by plasma treatment was used, the catalyst showed an improved total BTX selectivity compared to the fresh catalyst except for the first 10 minutes. Upon analysis of the results for each individual BTX compound, the selectivity for benzene was greatly increased by about 15% and the selectivity for xylene was increased by a few percentages (%), while the selectivity for toluene was slightly increased by about 1% (FIG. 11, Table 1 and Table 5 to Table 7).

In the present invention, the second step of regenerating a catalyst by plasma treatment may be achieved by dielectric barrier discharge (DBD). The "dielectric barrier discharge" means the electrical discharge between two electrodes which are separated by an insulating dielectric barrier. It is also called silent or inaudible discharge and is also known as ozone production discharge or partial discharge. In the device of the present invention, an alumina tube was used as the dielectric barrier.

In the present invention, as the acetylene-containing reactant gas used as a raw material, one which was prepared by supplying methane as a raw material to a plasma reactor and generating plasma by dielectric barrier discharge, may be used, but the acetylene-containing reactant gas is not limited thereto, and commercially available acetylene gas may be used. As described above, in the case where the acetylene is synthesized from methane in the plasma reactor to be used, the acetylene-containing reactant gas may also include by-products produced in the reaction process. Meanwhile, as the plasma reactor, the same device as the plasma reactor used in the second step of regenerating a catalyst by plasma treatment according to the present invention may be used, but the plasma reactor is not limited thereto. Meanwhile, the acetylene gas may be used alone or in the form of an inert gas and a mixed gas as along with hydrogen and nitrogen, but the form how the acetylene gas is used is not limited thereto.

In addition, the present invention can provide method of regenerating a zeolite catalyst for the aromatization of acetylene used in the synthesis of an aromatic compound from an acetylene-containing reactant gas, in which internal coke is formed inside the micropores of the zeolite catalyst and external coke is formed in the space between catalyst particles, outer surface of the particles, and/or empty space other than the micropores, and can be achieved by including following steps: (i) locating the used zeolite catalyst between a high voltage electrode and a ground electrode into a plasma reactor, in which the high voltage electrode is provided inside of the reactor and the ground electrode is provided outside of the reactor, and (ii) treating with the plasma generated by applying a voltage at the kV level to the high voltage electrode, so as to selectively remove 25 wt % to 50 wt % of the total amount of the external coke and 0.5 wt % to 10 wt % of the total amount of the internal coke from the zeolite catalyst.

In particular, the conditions of temperature and/or pressure for performing the regeneration method is as described above. The reaction may be performed with air flows, but conditions are not limited thereto.

As described above, the zeolite catalyst regenerated by the present invention may comprise cokes remaining at a ratio in the range of 0.5 to 0.7 (the amount of external coke/the amount of internal coke), but the ratio is not limited thereto, and may be appropriately adjusted so as to control the activity of the catalyst and/or the BTX selectivity to achieve the desired degree of a reaction speed.

The regenerated catalyst by such a method of the present invention can maintain the crystal structure of the zeolite catalyst itself before it is used in the reaction for the synthesis of an aromatic compound from an acetylene-containing reactant gas, in contrast to the catalyst regenerated by thermal treatment at high temperature. That is, even if the regeneration and the reaction are performed repeatedly, the regenerated catalyst can be structurally stable and can further maintain constant catalytic activity.

Furthermore, the present invention provides a zeolite catalyst for the aromatization of acetylene regenerated by the method of regenerating the zeolite catalyst for the aromatization of acetylene.

The regenerated catalyst of the present invention can provide adjusted activity of the catalyst during the subsequent aromatization of acetylene by containing an appropriate amount of coke inside the micropores. For instance, the regenerated catalyst is characterized in that it is adjusted so as to limit the initial explosive reaction and to delay it for performing a reaction over a long period of time by slightly lowering the activity of the catalyst by covering partial reactive acid sites with the coke remaining inside the micropores.

That is, by adjusting the catalyst in such a direction that the rate of the aromatization is reduced which results in the adjusted activity compared to a fresh catalyst, the acetylene conversion for the first 10 minutes of the reaction can be down-regulated to be in the range of 20% to 45%.

Additionally, the regenerated catalyst may show a BTX selectivity in the range of 40% to 55% in the aromatization of acetylene.

Furthermore, the present invention provides a dielectic barrier discharge (DBD) plasma reactor for regenerating a zeolite catalyst for the aromatization of acetylene used in the synthesis of an aromatic compound from an acetylene-containing reactant gas, in which internal coke is formed inside the micropores of the zeolite catalyst and external coke is formed in the space between catalyst particles, outer surface of the particles, and/or empty space other than the micropores. The plasma reactor of the present invention is characterized in that it comprises a channel-type container made of a dielectric material, which is able to receive the zeolite catalyst used in the aromatization of acetylene; a ground electrode, which is located on the outer wall of the channel-type container; a high voltage electrode, which is inserted into the zeolite catalyst received inside the channel-type container to be spatially separated in parallel from the channel-type container made of a dielectric material, and which has a higher voltage than the ground voltage; a fixing part, which fixes the used zeolite catalyst, that is received inside the channel-type container, in a predetermined area; and a power supply part, which provides a controlled voltage to the high voltage electrode, so as to selectively remove 25 wt % to 50 wt % of the total amount of the external coke and 0.5 wt % to 10 wt % of the total amount of the internal coke from the used zeolite catalyst.

In regenerating the deactivated catalyst by plasma treatment using the plasma reactor, for uniform plasma treatment over the catalyst received inside the reactor, the zeolite catalyst, which was used in the aromatization of acetylene, to be regenerated, may be supported by the fixing part to be received within the area covered with the ground electrode within the channel-type container, but the method of plasma treatment is not limited thereto.

Advantageous Effects of the Invention

The method of the present invention of removing cokes by plasma treatment that can be performed at ambient temperature and pressure and of regenerating a catalyst therefrom, lie in overcoming the drawbacks in the conventional method of thermal treatment at high temperature for regeneration of a catalyst, in which the coke may be completely removed, but the structure of the catalyst itself may be damaged, making it difficult to use the catalyst multiple times and resulting in excessive wasting of acetylene and forming a lot of cokes when the regenerated catalyst is used multiple times, again due to an initial explosive reaction, thus resulting in quick deactivation of the catalyst. Since the method of the present invention can be performed under mild conditions, the stability of the catalyst can be assured thus enabling repeated regeneration of the catalyst and the catalytic reaction. Additionally, since the reaction rate is adjusted by retaining a certain amount of the coke, a catalyst can be provided such that it can block the initial explosive reaction and subsequent side reactions as well as avoid excessive wasting of acetylene and deactivation by quick coking thus being able to prepare an aromatic compound with an improved BTX selectivity for a long period of time.

BRIEF DESCRIPTION OF DRAWINGS

FIG. 1 shows a schematic diagram of the dielectric barrier discharge (DBD) plasma system for the regeneration of the spent H-ZSM5 catalyst.

FIG. 2 shows TCD signal areas of CO and $CO_2$ of the spent H-ZSM-5 after regeneration by plasma at (a) 17.5 kV and (b) 20.0 kV.

FIG. 3 shows transmission electron microscopy (TEM) images of (a) the fresh H-ZSM-5, (b) the spent H-ZSM-5, (c) the plasma-regenerated H-ZSM-5 at 17.5 kV, and (d) the plasma-regenerated H-ZSM-5 at 20.0 kV.

FIG. 4 shows TEM images of (a) the thermally treated H-ZSM-5 at 800° C., (b) the spent H-ZSM-5 after regeneration by plasma at 17.5 kV, (c) the spent H-ZSM-5 after regeneration by plasma at 20.0 kV, and (d) the spent H-ZSM-5 after thermal treatment at 800° C.

FIG. 5 shows (A) Ar physisorption isotherm; (B) pore size distribution obtained by means of the H-K method; and (C) BJH pore size distribution obtained from adsorption branches of Ar physisorption for (a) the fresh H-ZSM-5, (b) the spent H-ZSM-5, (c) the plasma-regenerated H-ZSM-5 at 17.5 kV, (d) the plasma-regenerated H-ZSM-5 at 20.0 kV, and (e) the thermally treated H-ZSM-5 at 800° C.

FIG. 6 shows wide angle X-ray diffraction (XRD) patterns of (a) the fresh H-ZSM-5, (b) the spent H-ZSM-5, (c) the plasma-regenerated H-ZSM-5 at 17.5 kV, (d) the plasma-regenerated H-ZSM-5 at 20.0 kV, (e) the spent H-ZSM-5 after regeneration by plasma at 17.5 kV, and (f) the spent H-ZSM-5 after regeneration by plasma at 20.0 kV.

FIG. 7 shows thermogravimetric analysis (TGA) and differential thermal analysis (DTA) results of the spent H-ZSM-5, the plasma-regenerated H-ZSM-5 at 17.5 kV, the plasma-regenerated H-ZSM-5 at 20.0 kV, and the thermally treated H-ZSM-5 at 800° C.

FIG. 8 shows wide angle XRD patterns of (a) the thermally treated H-ZSM-5 at 800° C. and (b) the spent H-ZSM-5 after thermal treatment at 800° C.

FIG. 9 shows Fourier transform infrared spectroscopy (FT-IR) spectra of (a) the fresh H-ZSM-5, (b) the spent H-ZSM-5, (c) the plasma-regenerated H-ZSM-5 at 17.5 kV, (d) the plasma-regenerated H-ZSM-5 at 20.0 kV, and (e) the thermally treated H-ZSM-5 at 800° C. Asterisks designate a peak around 1580 $cm^{-1}$ to 1590 $cm^{-1}$, which can be ascribed to the C≡C stretching band derived from the presence of the graphitic coke on the samples.

FIG. 10 shows FT-IR spectra of (a) the spent H-ZSM-5 after regeneration by plasma at 17.5 kV, (b) the spent H-ZSM-5 after regeneration by plasma at 20.0 kV, and (c) the spent H-ZSM-5 after thermal treatment at 800° C. Asterisks designate a peak around 1580 $cm^{-1}$ to 1590 $cm^{-1}$, which can be ascribed to the C=C stretching band derived from the presence of the graphitic coke on the samples.

FIG. 11 shows catalytic performances of the fresh H-ZSM-5, the plasma-regenerated H-ZSM-5 at 17.5 kV, the plasma-regenerated H-ZSM-5 at 20.0 kV, and the thermally treated H-ZSM-5 at 800° C. (from left to right).

DETAILED DESCRIPTION OF THE INVENTION

Hereinafter, the present invention will be described in more detail with reference to the following Examples. However, these Examples are for illustrative purposes only and the scope of the invention is not limited by these Examples.

Example 1: Preparation and Characterization Analysis of the Catalyst for the Aromatization of Acetylene Commercialized conventional zeolite H-ZSM-5 (Zeolyst international Inc., USA) with Si/Al ratio of 15 was purchased for the catalyst in the aromatization of acetylene. Transmission electron microscopy (TEM) images of fresh H-ZSM-5, spent H-ZSM-5, and regenerated H-ZSM-5 were taken on the JEM-2100F field emission transmission electron microscope (FE-TEM, USA) under working voltage of 200 kV. X-ray diffraction (XRD) analysis was performed in the θ/2θ configuration using a Rigaku D/Max-2500V/PC diffractometer (Japan) with a Cu Kα radiation (40 kV, 200 mA, =0.154 nm) from 5° to 50°. Argon physisorption measurements were conducted at 87 K with an ASAP 2020 analyzer (Micromeritics, Inc., USA). Before the measurements, the samples were degassed at 623 K for 12 hours under vacuum condition. Fourier transform infrared spectroscopy (FT-IR) analysis were performed by using Nicolet iS50 (Thermo Fisher Scientific, Inc., USA) with potassium bromide pellet.

After the aromatization or the dielectric barrier discharge (DBD) plasma regeneration, the total weight of coke formed at the catalysts were measured by conducting thermogravimetric analysis (TGA). Specifically, all catalysts was heated from 40° C. to 800° C. with a ramping speed of 40° C.·min-1 under air (Q50, TA Instruments, USA; TGA 1, Mettler Toledo, USA). The weights of the internal and external cokes in the spent catalysts were calculated. With the estimated total cokes of all four samples from TGA data, the inventors further measured the Ar physisorption isotherms of the spent and regenerated catalysts, and determined their microporous volumes by the H-K method. By comparing micropore volumes of the spent and regenerated catalysts with that of the fresh catalyst, the inventors approximated the amount of coke formed inside the micropores by assuming that the decreased micropore volumes were occupied solely by coke. The internal coke amount was equal to the product of the decreased microporous volume and coke's density (1.22 g·cm$^{-3}$, please refer to Nature, 2009, 406: 246-249)

Example 2: Aromatization Reactor and Activity Test

The aromatization of acetylene was performed in a lab-made 2-channel micro fixed-bed reactor system. Each channel was constructed with 540 mm length and 10 mm inner diameter quartz tube. A spacer for loading catalysts was placed in the middle of quartz tube. The zeolite catalysts were loaded in the middle of the reactor and the zeolite catalysts were diluted (20 wt %) with ball-type alumina ($\alpha$-Al2O3, ø=1 mm). The aromatization was performed at 650° C. and atmospheric pressure. The composition of feed was $C_2H_2$:$H_2$:$N_2$=1:2:7 with gas hourly space velocity (GHSV) of 20,000 mL·$g_{cat}^{-1}$·$h^{-1}$.

On-line Gas Chromatography (6500GC Young Lin Instrument Co., Korea) was used to analyze the products from the reaction. The on-line GC employs Porapak-Q columns and a Molecular Sieve 5A connected with a thermal conductivity detector (TCD), and a Gas-pro column connected with a flame ionization detector (FID). $H_2$, $N_2$, and $CH_4$ in the products were detected by using the TCD, and hydrocarbons such as $CH_4$, $C_2H_6$, $C_2H_4$, $C_2H_6$, $C_3H_8$, $C_3H_6$, benzene, toluene, and xylene (ortho-, meta-, para-) were detected by using the FID. An acetylene conversion and a benzene, toluene and xylene (BTX) selectivity according to the reaction time were shown in Table 1 below. As shown in Table 1, from 90 minutes after the initiation of the reaction, the changes in the acetylene conversion and BTX selectivity were slow, and no further changes were observed after 130 minutes.

TABLE 1

| | TOS (min) | Acetylene conversion (%) | Selectivity (%) | | | |
|---|---|---|---|---|---|---|
| | | | Benzene | Toluene | Xylene | BTX |
| H-ZSM-5 (Si/Al = 15) at 650° C. | 10 | 99.95 | 32.65 | 21.1 | 4.79 | 58.54 |
| | 50 | 32.43 | 19.81 | 4.51 | 5.98 | 30.3 |
| | 90 | 22.46 | 26.61 | 3.19 | 7.62 | 40.42 |
| | 130 | 20.8 | 31.97 | 3.1 | 8.03 | 43.1 |
| | 170 | 20.27 | 32.81 | 2.89 | 7.85 | 43.55 |

Example 3: DBD Plasma Bed for Regeneration

A DBD plasma regeneration was performed at atmospheric pressure with aeration and near room temperature. The schematic diagram for this device was illustrated in FIG. 1. GHSV was 1500 mL·mL·$g_{cat}^{-1}$·$h^{-1}$ with feed of air and time for the regeneration was 720 min. FIG. 1 shows the lab-made DBD plasma system. An alumina tube of 6 mm internal diameter and 2 mm thickness was used as a dielectric barrier for the plasma bed. A 3 mm diameter stainless steel rod was used as a high voltage electrode, and a steel wire was used as a ground electrode. The 150 mm length discharge zone was covered with the ground electrode. The discharge gap between inner surface of the alumina tube and the high voltage electrode was 1.5 mm, and the spent H-ZSM-5 catalyst was densely packed in this region for the regeneration. A sinusoidal AC power supply (0 V to 220 V, 60 Hz to 1,000 Hz) was connected to a transformer (0-20 kV, 1,000 Hz), and this electrical system continuously applied high voltage to the plasma bed. The applied voltage to the plasma bed was varied from 17.5 kV to 20.0 kV, and the frequency was fixed as 1 kHz. A capacitor with 1 μF capacitance was connected in series between the plasma bed and the ground. A high voltage probe (1,000:1, P6015A, Tektronix) for the high voltage electrode and a voltage probe (10:1, P6100, Tektronix) for the ground electrode were connected to a digital oscilloscope (TDS 3012C, Tektronix), and each voltage was measured.

The effluent gas from the plasma bed was analyzed by on-line gas chromatography (6500GC Young Lin Instrument Co., Korea) employing a Porapak-N and a Molecular Sieve 13X columns connected with a thermal conductivity detector (TCD). $O_2$, $N_2$, CO and $CO_2$ in the effluent were detected by using the TCD. The elution profiles of CO and $CO_2$ at 17.5 kV and 20.0 kV were shown in FIG. 2.

For comparison, some amount of the spent H-ZSM-5 sample was placed to a muffle furnace. A thermal treatment for the sample was then conducted at 800° C. for 5 h at the ramping speed of 10° C. min$^{-1}$.

Experimental Example 1: TEM Image Analysis and Physisorption Methods

TEM imaging analysis was conducted with the fresh, the spent, and the DBD plasma-treated H-ZSM-5 after aromatization, and the results are shown in FIG. 3. As seen in FIG. 3, the amount of coke was slightly removed inside the micropores at 17.5 kV, and the removed amount was further increased at 20.0 kV. FIG. 4 additionally shows the TEM images of the thermally treated H-ZSM-5 at 800° C., the spent H-ZSM-5 after regeneration at 17.5 kV, the spent H-ZSM-5 after regeneration at 20.0 kV, and the spent H-ZSM-5 after thermal treatment at 800° C. From the viewpoint of coke removal only, the thermal treatment was found a more efficient method because there remained a very small amount of coke after this treatment (FIG. 4a vs. FIGS. 3c and 3d). Even though the spent catalyst treated by either plasma or heat, the carbonaceous materials were spotted inside pores and around the particles after the 2$^{nd}$ run of aromatization (FIGS. 4b to 4d).

Table 2 shows the results of Ar physisorption. The BET surface area, the outer surface area, and the volume of micropores are shown. After the aromatization from acetylene at elevated temperature, a lot of carbon deposition formed and the BET surface area decreased significantly by 96.4%, from 402 m$^2$/g to 14.4 m$^2$/g. Consequently, the pore volume of 0.132 cm$^3$/g decreased down to 0.00317 cm$^3$/g. The difference in volume could be ascribed to the volume of carbon deposited inside the micropores. The spent catalyst was first treated with the DBD plasma at 17.5 kV and 1 kHz and $S_{BET}$, $S_{ex}$ and $V_{micro}$ were slightly changed. When the plasma power increased to 20.0 kV at the same frequency level, $S_{BET}$, $S_{ex}$, and $V_{micro}$ increased 2.63 times, 1.85 times, and 3.31 times compared with the spent catalyst, respectively. For comparison, the inventors have conducted a thermal treatment with the spent catalyst at 800° C. with aeration. The remaining amount of carbon deposition at thermally regenerated catalyst seemed to be negligible by comparing $V_{micro}$ volumes between the treated and fresh H-ZSM-5 ones. The thermal treatment apparently seemed to be a very effective way to remove carbon deposition, however, more closely looking into the decrease in $V_{micro}$ and the increase in $S_{ex}$ revealed compared with those of the fresh catalyst that the changes were believed to be the result of structural modification or damage. According to Catalysis today (2011, 178: 72-88), a similar kind of thermal treatment at elevated temperature for regeneration could damage the aluminum framework, elucidated by employing $^{27}$Al MAS NMR spectroscopy. They pointed out that the peak intensity at around 54 ppm was decreased and a new peak near 0 ppm appeared, indicating the tetrahedrally coordinated alumina framework was damaged, and octahedrally coordinated Al atoms were formed out of the zeolite framework, respectively. Therefore, the inventors believe that the damaged framework and the dealuminated fraction due to thermal treatment made extra empty space other than the micropores in the original framework, leading to a significant increase in $S_{ex}$ (outer surface area of particles and induced surface area due to newly formed empty space inside the particles) nearly 1.56 times. Because of this, the microporous structure in the framework also seemed slightly damaged, and the $V_{micro}$ and $S_{BET}$ was decreased by 0.009 cm$^3$/g and 15 m$^2$/g, respectively.

TABLE 2

| Samples | $S_{BET}$ (m$^2 \cdot$g$^{-1}$) | $S_{ex}^a$ (m$^2 \cdot$g$^{-1}$) | $V_{micro}^b$ (cm$^3 \cdot$g$^{-1}$) |
|---|---|---|---|
| Fresh H-ZSM-5 | 402 | 39.1 | 0.132 |
| Spent H-ZSM-5 | 14.4 | 13.7 | 0.00317 |
| Regenerated H-ZSM-5 at 17.5 kV | 15.7 | 11.8 | 0.00374 |
| Regenerated H-ZSM-5 at 20.0 kV | 37.9 | 25.4 | 0.0105 |
| Thermally treated H-ZSM-5 at 800° C. | 387 | 60.9 | 0.123 |

$^a$t-calculated by t-plot method.
$^b$calculated by H-K method.

FIG. 5 shows the results of physisorption isotherms (A), pore size distribution of micropores (B), and mesopores (C). As shown in FIG. 5A, all the samples seemed to have mostly micropores. FIG. 5B shows the size distribution ranging from 0.4 to 0.6 nm, which is close to the channel size of H-ZSM-5 (about 0.5 nm). It was found that the micropores of the spent and the regenerated at 17.5 kV seemed entirely filled with carbonaceous material (FIGS. 5B(b and c)). When the plasma power was increased to 20.0 kV, the coke inside the micropores was removed to some degree (FIG. 5B(d)). In the case of the thermal treatment (FIG. 5B(e)), almost all the coke seemed eliminated, however, the microporous volume was slightly decreased.

In addition, the inventors have further investigated the mesoscale pores and showed the result in FIG. 5C. The amount of this kind of pores was relatively small, but the inventors could detect the changes after the reaction and each treatment. As expected, the pore volume of the spent catalyst was greatly decreased (FIG. 5C(b)). When the DBD plasma at 17.5 kV was applied, the amount of coke removal was negligible at this scale (FIG. 5C(c)). When the power was increased to 20.0 kV, a slight amount of coke was removed (FIG. 5C(d)). It was very interesting that the thermally treated one (FIG. 5C(e)) was found to have more pore space than that of the original fresh catalyst (FIG. 5C(a)). This seemed to be the result of similar structural change as seen in the microporous region. Simultaneously considering the additional observations discussed in later sections (specifically, XRD, FT-IR, and TGA), the decrease in microporous volume and the increase in mesoporous volume were possibly due to the structural modification or damage in the thermally treated sample (FIG. 5e).

Table 3 summarizes the amounts of internal coke formed inside the micropores and the external coke formed elsewhere at such spaces between particles, the space close to the outer surface of particles, and the induced void fraction due to chemical reaction and regeneration processes. By using this volume difference and the density of carbon, the amount of internal coke could be calculated, and the amount of external coke corresponded to the amount difference between the total coke and the internal coke. In the case of the spent H-ZSM-5, $V_{micro}$ was very small compared to $V_{micro\ fresh}$, indicating that almost all micropores seemed filled with carbonaceous material. The amount of external coke was estimated to be 0.84 times the amount of internal coke. When treated with the DBD plasma at 17.5 kV, the amount of total coke was decreased from 0.290 g·zeolites g$^{-1}$ to 0.248 g·zeolites g$^{-1}$, mostly due to the decrease in external coke. The removed amount of internal coke seemed very small. In contrast, when treated at 20.0 kV, $V_{micro}$ increased and the amount of coke was significantly removed. The effect on the removal of external coke was shown to be more pronounced. At the comparative run, 92.4% of internal coke was burnt off and the amount of total coke decreased down to 0.012 g·zeolites g$^{-1}$. Actually, no trace of external coke was observed.

TABLE 3

| Samples | $V_{micro}^a$/ $V_{micro}^b$ (%) | Total coke (g · zeolites g$^{-1}$) | Internal coke (g · zeolites g$^{-1}$) | External coke (g · zeolites g$^{-1}$) | External coke/internal coke |
|---|---|---|---|---|---|
| Spent H-ZSM-5 | 2.39 | 0.290 | 0.158 | 0.132 | 0.84 |
| Regenerated H-ZSM-5 at 17.5 kV | 2.82 | 0.248 | 0.157 | 0.091 | 0.58 |
| Regenerated H-ZSM-5 at 20.0 kV | 7.96 | 0.234 | 0.149 | 0.085 | 0.57 |
| Thermally treated H-ZSM-5 at 800° C. | 92.6 | 0.012 | 0.012 | 0.000 | 0.00 |

$^a$Micropore volume of zeolites after catalytic activity test or regenerated treatment obtained by H-K method.
$^b$Micropore volume of fresh zeolites obtained by H-K method.

Considering the results of Tables 1 and 2, the inventors believe that this DBD plasma treatment could be more successfully applied when carbon depositions located on the outer surfaces and in the space between particles, rather than inside the micropores whose dimension seems far below the optimum range for microdischarge and streamer generated by the DBD plasma technique.

Experimental Example 2: X-Ray Diffraction Method

In FIG. 6, the results of fresh, spent, regenerated, and spent after regenerated H-ZSM-5 catalysts are shown. As shown in FIG. 6a, the characteristic peaks of the fresh H-ZSM-5 were clearly seen and easily identified compared with the reference spectrum generated by the single crystal software Mercury 3.7. After the aromatization at elevated temperature in FIG. 6b, the structure of the spent H-ZSM-5 appeared well maintained and unchanged except for the peak at 26.4°, which is known to be a peak of crystalline graphite carbon. The carbon peak could be ascribed to the coke deposited around the particles and inside pores of the zeolite catalyst. Considering the results of TGA in FIG. 7, the carbonaceous materials must have been a mixture of crystalline and amorphous carbons since the decomposition temperature ranged from 600° C. to 800° C. This XRD spectrogram well explained the existence of crystalline graphite components formed during the aromatization. In order to regenerate the spent H-ZSM-5 with carbon depositions, the inventors applied the DBD plasma by adjusting the power supply. At 17.5 kV of supply power (FIG. 6c), the peak intensity for the coke near 26.4° seemed unchanged, however, the intensity in the case of 20.0 kV did decrease (FIG. 6d). It is believed that the increased energy delivered by plasma helped remove the crystalline coke to some extent. With this regenerated zeolite, the aromatization was carried out again at the same reaction condition for the same reaction time. The XRD results of the spent H-ZSM-5 after regeneration at 20.0 kV was shown in FIG. 6e. As shown in FIG. 6e, the intensity of graphite carbon did not seem to change, indicating no further crystalline graphite formed during the 2nd run of the aromatization. The additional amount of coke formed at the $2^{nd}$ run was found quite small as shown in Table 4. In contrast, nearly the same amount of coke was formed again (22.80 wt % vs. 22.49 wt %) in the case of the thermally treated sample in comparison with the spent H-ZSM-5 after the 1st aromatization run (first sample in Table 4). It was also clearly verified through the XRD method, and the result was shown in FIG. 8. This indicates that the remaining coke after the plasma treatment blocks further formation of graphite-like coke materials. It was believed that this phenomenon prevented the significant wasting of acetylene towards graphite-like coke and maintained the BTX selectivity although the remaining carbon deposition might have compromised catalytic activity by partially preoccupying or covering acid sites.

TABLE 4

| Samples | Weight loss (%) | Additional amount of coke formed in the $2^{nd}$ run after each treatment (wt %)* |
|---|---|---|
| Spent H-ZSM-5 | 22.49 | — |
| Regenerated H-ZSM-5 at 17.5 kV | 19.85 | 7.54 |
| Regenerated H-ZSM-5 at 20.0 kV | 18.93 | 6.57 |
| Thermally treated H-ZSM-5 at 800° C. | 1.19 | 22.80 |

*Amount of coke generated = amount of coke formed – amount of coke remaining in the treated sample For comparison, the inventors regenerated the spent H-ZSM-5 by conducting a traditional thermal treatment of the spent H-ZSM-5 by supplying thermal heat and air flows. The XRD results after the treatment showed that there existed nearly no crystalline coke. For the purpose of graphite-like coke removal only, this thermal treatment definitely was an improve method. However, when a $2^{nd}$ aromatization over this catalyst regenerated by the thermal treatment was conducted, practically the similar amount of graphite-like coke was also generated, which caused a waste of acetylene, a raw material for the aromatization, and deactivation of the catalyst as well. Looking into the results of the regenerated catalysts treated with the DBD plasma, the selectivity towards aromatics still remained at similar ranges, and the abrupt initial decrease in conversion could be avoided. Reportedly, a better structural stability was achieved when the DBD plasma was chosen in comparison with the thermal treatment at elevated temperature.

Experimental Example 3: Analysis of Carbonaceous Residue Materials by TGA, DTA & FT-IR Methods As shown in the result of TGA in FIG. 7, the amount of coke in samples in decreasing order was found: the spent H-ZSM-5, the regenerated H-ZSM-5 at 17.5 kV DBD plasma, and the regenerated H-ZSM-5 at 20.0 kV DBD plasma. It seemed obvious that higher power applied to the bed could eliminate more carbon materials. Regarding the result of DTA, the most intense peak of DTA curve in the case of the regenerated H-ZSM-5 at 20.0 kV DBD plasma was observed around 688° C., which was lower than the peak temperature (ca. 701° C.) of different samples by 13° C. We believe that more intense power could eliminate more coke materials, and partially turn solid crystalline carbons into more easily decomposable and removable carbon species. Furthermore, the inventors also conducted the $2^{nd}$ aromatization runs at the same reaction condition after each treatment described. The result of TGA was shown in Table 4. As shown in Table 4, the amount of additional coke by the $2^{nd}$ run seemed quite small compared with the amount of coke from the thermally treated sample at 800° C. The remaining carbon material partially covering the acidic surface seemed to have suppressed excessive side reactions by keeping moderate level of conversion, especially at the very early stage.

FIG. 9 shows the FT-IR spectra of the fresh, the spent, the plasma-treated, and the thermally treated catalyst samples. Different from the fresh catalyst, the peak at 1580 cm$^{-1}$ to 1590 cm$^{-1}$ appeared in all the spent catalysts, regardless of the number of runs. The FT-IR results after the $2^{nd}$ aromatization run were additionally shown in FIG. 10. This peak, reportedly, can be ascribed to the C=C stretching band, whose source was definitely the graphitic coke materials in the spent catalysts. This peak seems different from the peak at the slightly higher band of ca. 1640 cm$^{-1}$, which seemed to be caused by water adsorption. Regarding the regenerated samples by the DBD plasma, the C=C stretching bands were observed, while the thermally treated sample at 800° C. did not show any trace of this stretching.

It was found that the existence of in-plane aromatic C—H deformation mode was vaguely observed at 1,440 cm$^{-1}$ except for the fresh and the thermally treated samples, whereas aromatic C—H group (3,000 cm$^{-1}$ to 3,100 cm$^{-1}$) and out-of-plane aromatic C—H deformation mode (870 cm$^{-1}$, 820 cm$^{-1}$, and 755 cm$^{-1}$) were barely seen. Considering the stretching mode and the results of the thermogravimetric analysis, the species of coke seemed to be pseudo-graphite cokes.

Experimental Example 4: Catalytic Performance

A series of aromatization runs were conducted and 4 data sets are shown in FIG. 11. The reactions were conducted using the catalysts, which were regenerated by plasma treatment at 17.5 kV and 20.0 kV, respectively, according to a method of regeneration of the present invention, and the thermally regenerated H-ZSM-5 at 800° C. as another Comparative Example. The specific numbers of acetylene conversion, selectivity for an individual BTX compound, and total BTX selectivity specifically measured for these 3 kinds of samples are shown in Tables 5 to 7, respectively. Furthermore, the inventors compared the results with Table 1 which shows the results of the aromatization of acetylene using the fresh H-ZSM-5 conducted as a control group. In the case of fresh catalyst, the acetylene conversion was very high initially and abruptly dropped down to the level of about 20% within 2 h. The acetylene was so reactive at 650° C., and the consumption rate was very fast. In the case of severe deactivation of catalysts, many researchers tried to overcome the problem by incorporating mesoporosity and modifying surface characteristics physically and chemically. The other reasonable option could be a regeneration of catalyst by eliminating carbonaceous materials at a certain interval. The easiest way is to burn all the coke formed in the zeolite catalyst by heating and aeration at elevated temperature, normally over 800° C. However, this heat treatment may lead to the structural damage of a catalyst and requires a lot of energy. Even worse, the lifetimes of a catalyst and reaction system devices are subject to be shortened. In the aromatization over regenerated H-ZSM-5 by thermal treatment at 800° C., the conversion dropped remarkably at very early stage, which seemed similar to the test run with the fresh catalyst. This indicates that a lot of acetylene was wasted due to side reactions to form coke even though the valuable BTX were simultaneously synthesized from acetylene. Useless wasting of acetylene especially at the early stage could be avoided by using mildly regenerated catalyst, which could be achieved by applying the DBD plasma at ambient temperature and pressure. In addition, this mild technique hardly harmed the structure of the original catalyst as shown in the results of physisorption and XRD.

TABLE 5

| | TOS (min) | Acetylene Conversion (%) | Selectivity (%) | | | |
|---|---|---|---|---|---|---|
| | | | Benzene | Toluene | Xylene | BTX |
| Regenerated H-ZSM-5 at 17.5 kV (Si/Al = 15) at 650° C. | 10 | 29.52 | 22.31 | 3.57 | 7.48 | 33.36 |
| | 50 | 19.66 | 34.37 | 3.76 | 10.84 | 48.97 |
| | 90 | 19.06 | 35.62 | 3.84 | 10.98 | 50.44 |
| | 130 | 18.6 | 36.67 | 3.89 | 10.98 | 51.54 |
| | 170 | 18.74 | 36.09 | 3.78 | 10.18 | 50.05 |

TABLE 6

| | TOS (min) | Acetylene Conversion (%) | Selectivity (%) | | | |
|---|---|---|---|---|---|---|
| | | | Benzene | Toluene | Xylene | BTX |
| Regenerated H-ZSM-5 at 20.0 kV (Si/Al = 15) at 650° C. | 10 | 35.77 | 19.3 | 5.27 | 5.56 | 30.13 |
| | 50 | 21.52 | 32.46 | 3.54 | 7.7 | 43.7 |
| | 90 | 21.13 | 33.02 | 3.2 | 7.66 | 43.88 |
| | 130 | 19.47 | 36.55 | 3.52 | 8.03 | 48.1 |
| | 170 | 19.2 | 36.96 | 3.64 | 8.24 | 48.84 |

TABLE 7

| | TOS (min) | Acetylene Conversion (%) | Selectivity (%) | | | |
|---|---|---|---|---|---|---|
| | | | Benzene | Toluene | Xylene | BTX |
| Thermally treated H-ZSM-5 at | 10 | 65.08 | 18.99 | 17.86 | 10.57 | 47.42 |
| | 50 | 33.65 | 22.15 | 5.21 | 6.48 | 33.84 |

TABLE 7-continued

| | TOS (min) | Acetylene Conversion (%) | Selectivity (%) | | | |
|---|---|---|---|---|---|---|
| | | | Benzene | Toluene | Xylene | BTX |
| 800° C. (Si/Al = 15) at 650° C. | 90 | 27.37 | 25.11 | 4.05 | 6.55 | 35.71 |
| | 130 | 23.89 | 27.48 | 3.56 | 7.24 | 38.28 |
| | 170 | 21.53 | 30.01 | 3.26 | 7.97 | 41.24 |

With respect to the selectivities of aromatics, the selectivity levels of benzene, toluene, and xylene were found slightly different from each other, but as shown in FIG. 11, the difference was not quite big in the cases of all catalyst samples after a few sampling points. At very early stage before 1 h, the BTX selectivity of fresh catalyst was very high, and that of thermally treated H-ZSM-5 at 800° C. also showed comparably high selectivity. In contrast, the initial BTX selectivity was the lowest in the cases of regenerated zeolites treated with plasma at 17.5 kV and 20.0 kV. After the first sampling period, the BTX selectivity was increased to the level of 45% to 50% for both cases. The abrupt drop of conversion was successfully avoided, the initial conversion changes (difference between the first and the second conversions) were 9 percentage points and 12 percentage points for the second and the third samples, respectively. In the cases of fresh and thermally treated samples, the initial conversion changes were 65 percentage points and 31 percentage points. For the plasma-regenerated samples, the BTX were produced slightly more after the first sampling point, since the excessive side reactions were successfully avoided. Among the BTX products, the benzene selectivity was shown relatively high. We believe that the narrowed micropores of H-ZSM-5 caused by the remaining coke possibly exerted an influence on increasing the benzene selectivity, relatively limiting the formation of larger aromatics due to the geometrically confined environment.

The relative compositions of BTX and their profiles with time in the case of thermally treated catalyst at 800° C. appeared very similar to the results of its original one, i.e., fresh catalysts.

A non-thermal, dielectric barrier discharge (DBD) plasma was successfully applied to the deactivated H-ZSM-5 catalyst bed for regeneration. By adjusting the strength of discharge power, the amount of coke eliminated was accordingly controlled. Unlike the conventional thermal treatment, this plasma treatment barely harmed the original crystalline and nanoporous structure of H-ZSM-5 catalyst. In addition, the mildly treated and regenerated catalyst by plasma showed comparable BTX selectivity to the fresh one. Due to the more restricted microporous environment, the formation of relatively smaller benzene seemed more favored at internal acid sites. It should be noted that the plasma-regenerated catalyst suppressed the excessive wasting of acetylene caused by enormous coke especially at very early stage of aromatization, keeping the comparable BTX selectivity while compromising the level of conversion. Furthermore, the plasma-regenerated catalysts showed a better structural stability and higher BTX selectivity than the thermally regenerated catalyst at elevated temperature.

The invention claimed is:
1. A method for preparing an aromatic compound from acetylene, the method comprising the following steps:
   1) synthesizing an aromatic compound from an acetylene-containing reactant gas in the presence of a zeolite catalyst for aromatization of acetylene, thereby forming internal coke inside micropores of the zeolite catalyst and external coke in space between catalyst particles, outer surface of the particles, and/or empty space other than the micropores;

2) (i) locating the zeolite catalyst used in step 1) between a high voltage electrode and a ground electrode, wherein the high voltage electrode is provided inside a plasma reactor and the ground electrode is provided outside the plasma reactor, and (ii) treating the zeolite catalyst with plasma generated by applying a voltage at a kV level to the high voltage electrode, so as to selectively remove 25 wt % to 50 wt % of the total amount of the external coke and 0.5 wt % to 10 wt % of the total amount of the internal coke from the zeolite catalyst, thereby producing a plasma-treated zeolite catalyst, wherein a ratio of an amount of external coke to an amount of internal coke in the plasma-treated zeolite catalyst is from 0.5 to 0.7; and 3) using the plasma-treated zeolite catalyst as the zeolite catalyst for the aromatization of acetylene in step 1).

2. The method of claim 1, wherein step 2) is performed by applying a voltage in the range of 7 kV to 50 kV to the high voltage electrode.

3. The method of claim 1, wherein step 2) and step 3) are repeated n times, wherein n is a positive integer.

4. The method of claim 1, wherein the external and internal cokes removed by the plasma treatment are graphitic carbonaceous materials.

5. The method of claim 1, wherein the plasma-treated zeolite catalyst show an acetylene conversion of 20% to 45% by weight for an initial period of 10 minutes in the aromatization of acetylene of step 3).

6. The method of claim 1, wherein the plasma-treated zeolite catalyst shows a benzene, toluene, and xylene selectivity of 40% to 55% by weight in the aromatization of acetylene of step 3).

7. The method of claim 1, wherein step 2) is achieved by dielectric barrier discharge.

8. The method of claim 1, wherein the method further comprises:
supplying methane to a plasma reactor,
generating plasma by dielectric barrier discharge; and
reacting the methane to produce the acetylene-containing reactant gas.

9. The method of claim 8, wherein the plasma reactor for producing the acetylene-containing reactant gas is also used as the plasma reactor for treating the zeolite catalyst with plasma in step 2).

* * * * *